United States Patent
Garcia et al.

(10) Patent No.: US 7,496,479 B2
(45) Date of Patent: Feb. 24, 2009

(54) SYSTEM FOR MONITORING PATIENT SUPERVISION BY HEALTH-CARE WORKERS

(75) Inventors: Luis Garcia, Slinger, WI (US); Bryan D. Dickerson, Hartford, WI (US); Jeffrey A. Kuhlow, Fond du Lac, WI (US); Gary C. Sutcliffe, Slinger, WI (US); Jeffrey H. Peterson, Jackson, WI (US); Michael D. Cook, Watertown, WI (US); Nathan A. Schleifer, Grafton, WI (US)

(73) Assignee: API Software, Inc., Hartford, WI (US)

( * ) Notice: Subject to any disclaimer, the term of this patent is extended or adjusted under 35 U.S.C. 154(b) by 280 days.

(21) Appl. No.: 11/459,125

(22) Filed: Jul. 21, 2006

(65) Prior Publication Data

US 2007/0083445 A1    Apr. 12, 2007

Related U.S. Application Data (63) Continuation-in-part of application No. 11/207,446, filed on Aug. 19, 2005.

(51) Int. Cl.
   *G06F 11/00* (2006.01)
(52) U.S. Cl. .................................................. 702/188
(58) Field of Classification Search .............. 702/188; 340/286.07
   See application file for complete search history.

(56) References Cited

U.S. PATENT DOCUMENTS

| | | | |
|---|---|---|---|
| 5,838,223 A * | 11/1998 | Gallant et al. | 340/286.07 |
| 5,960,085 A | 9/1999 | de la Huerga | |
| 6,681,003 B2 | 1/2004 | Linder et al. | |
| 6,749,566 B2 | 6/2004 | Russ | |
| 6,779,024 B2 | 8/2004 | de la Huerga | |
| 6,871,211 B2 | 3/2005 | Labounty et al. | |

* cited by examiner

*Primary Examiner*—Tung S Lau
*Assistant Examiner*—Stephen J Cherry
(74) *Attorney, Agent, or Firm*—Quarles & Brady LLC; George E. Haas (57) ABSTRACT

A monitoring system in a medical facility provides an identification device to a patient and a data acquisition device to a health-care worker. The identification device wirelessly emits a first signal that identifies the patient and the data acquisition device emits a second signal. A determination is made in response to the first signal and the second signal, whether the health-care worker is absent from being near the patient. For example, absence of the health-care worker is determined when a data reader receives only the first signal. This system detects when a patient requiring continuous observation is not in the presence of a health-care worker. In that case, an alarm message is sent to supervisory personnel.

24 Claims, 3 Drawing Sheets

SYSTEM FOR MONITORING PATIENT SUPERVISION BY HEALTH-CARE WORKERS

CROSS-REFERENCE TO RELATED APPLICATIONS

This is a continuation in part of U.S. patent application Ser. No. 11/207,446 filed on Aug. 19, 2005.

STATEMENT REGARDING FEDERALLY SPONSORED RESEARCH OR DEVELOPMENT

Not Applicable

BACKGROUND OF THE INVENTION

1. Field of the Invention

The present invention relates to time and attendance systems for monitoring employee work hours at a medical facility, and more particularly to a computer system which monitors whether a patient is in the presence of a health-care worker at predefined times or locations.

2. Description of the Related Art

Health-care workers at a medical facility have historically used a time clock to record the time of day on an attendance card upon entering and exiting the workplace. Today computerized time and attendance systems have replaced the traditional time clocks. These systems read an unique employee number and other data from an identification badge when the employee arrives and departs the workplace. The acquired employee identification data are transmitted and recorded in a central computer along with the current date and time. That recorded information is subsequently used by a payroll program to calculate the amount of wages that each employee is to receive.

The employee identification badge also may be used to unlock doors to restricted areas of the medical facility, such as a pharmacy or psychiatric ward. This not only limits access to those areas, it also monitors which employees entered and when.

More recently, as described in the related patent application, another monitoring system for a medical facility has been developed which tracks the amounts of time that different health-care workers spend attending to each patient. That system locates an identification device near each patient, such as by embedding the device in a patient wrist band or in a chart held on the patient's bed. A data acquisition device is carried by health-care workers, such as physicians, nurses, physical therapists and the like, who directly provide care to the patients. When the health-care worker is in close proximity to a patient (e.g. within 10 feet), the worker's data acquisition device receives a signal from the identification device and measures an amount of time that the signal for that identified patient is received. This enables the data acquisition device to record which patients that health-care worker treats and the duration of each treatment.

A data interrogator occasionally reads the recorded data from each health-care worker's data acquisition device which identify the associated health-care worker, the patients that were treated, and the amount of treatment time. The data so read can be used to prepare reports for each patient specifying the amount of treatment received from each class of health-care worker, how frequently treatment was administered and other treatment related information. The patient reports are useful for billing and treatment monitoring purposes. The acquired data also can be used to generate reports about each health-care worker which provide information related to which patients were treated and the amount of time spent attending to patients. Knowing additional information about the acuity or ailment of each patient enables administrative personnel to determine the amount of treatment time various types of patients or ailments require from each class of health-care worker.

SUMMARY OF THE INVENTION

A method for monitoring supervision of a patient by medical personnel comprises issuing an identification device to the patient wherein the identification device wirelessly emits a first signal that identifies the patient. A data acquisition device, issued to a health-care worker, emits a second signal. A determination is made, in response to the first signal and the second signal, regarding attendance of the health-care worker near the patient. Preferably, the health-care worker being absent from being near the patient is detected and an alarm message is transmitted to a nursing supervisor.

In one version of the monitoring method, the first signal identifies the patient and is received by the data acquisition device issued to a health-care worker. The first signal continues to be received as long as the health-care worker is in close proximity to the patient, but due to a short transmission range that signal is not received when the health-care worker is remote from the patient. The data acquisition device records either the time period that the first signal is received or the absence of receipt of the first signal. That recorded information is used in generating the second signal which conveys an indication of the presence or absence of the health-care worker near the patient. The second signal is received by a data reader in the medical facility and used to determine whether the patient is being continuously observed by the health-care worker.

In another version of the monitoring method, the first signal, identifying the patient, is received directly by the data reader. The data reader also receives the second signal from the data acquisition device issued to a health-care worker. Because both the first and second signals have relatively short transmission ranges, the nearly simultaneous receipt of both signals indicates that the health-care worker and the patient are in close proximity to each other. Thus the receipt of only one of the first and second signals indicates that the health-care worker and the patient are apart from each other.

With either version, a plurality of data readers can be located throughout the medical facility. This enables monitoring to continue as the patient is escorted around the facility by a health-care worker.

DETAILED DESCRIPTION OF THE INVENTION

Figure 1:
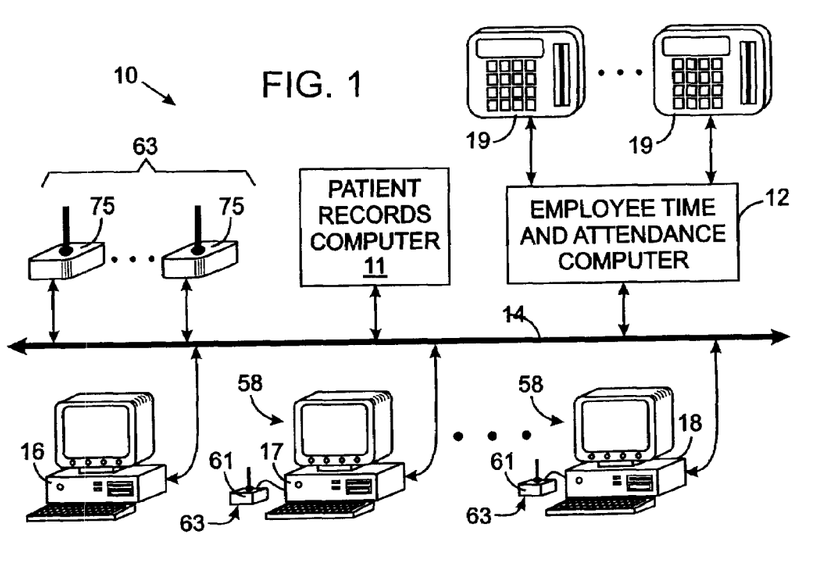
FIG. 1 is a schematic diagram of a hospital computer system which stores patient records, as well as information about hospital employees.

FIG. 1 illustrates a computer system 10 of a medical facility, such as a hospital. Although the present invention is being described in the context of a hospital, the inventive concepts can be applied to other patient care facilities, such as clinics, nursing homes and extended care facilities for example. The computer system 10 includes a computer 11 that processes and stores patient records and a time and attendance computer 12 which executes software programs that schedule work periods for employees and then records the actual amounts of time each employee works. The patient records computer 11 and the time and attendance computer 12 are connected to a conventional local area network (LAN) 14 of a type commonly found in work places. A plurality of personal computers 16, 17 and 18 are connected to the local area network 14 to exchange data and commands with the computers 11 and 12. It should be understood that many more personal computers than are illustrated are connected to the LAN 14 throughout the hospital. For example, personal computers are located at nursing stations, treatment areas, and administrative offices.

For processing employee time and attendance data, a plurality of badge readers 19, through which employees indicate when they start and end periods of work, are located throughout the hospital and are connected to the local area network 14. The badge readers 19 can take any of a number of commercially available forms. For example, each employee is issued an identification badge (badge 13 in FIG. 2) that has a magnetic strip which encodes a unique employee identifier (e.g. identification number) and the magnetic strip is read when the employee swipes the identification badge through a slot of a badge reader 19. Each badge reader also has a keypad by which an employee identifier or other information can be entered into the time and attendance computer 12. A display screen on each badge reader 19 presents information to the employee.

When a patient enters the hospital, an admissions office worker inputs information into the patient records computer 11 via one of the personal computers 16. This process creates a record for that patient for this particular visit within the memory of the patient records computer 11. That record contains standard information, such as the patient's name, address, biographical information, billing information, healthcare workers' names and the like. As is conventional practice in most medical facilities, the personal computer 16 prints a label 15 for a wristband that is worn by the patient to provide identification of this patient to healthcare workers.

Figure 2:
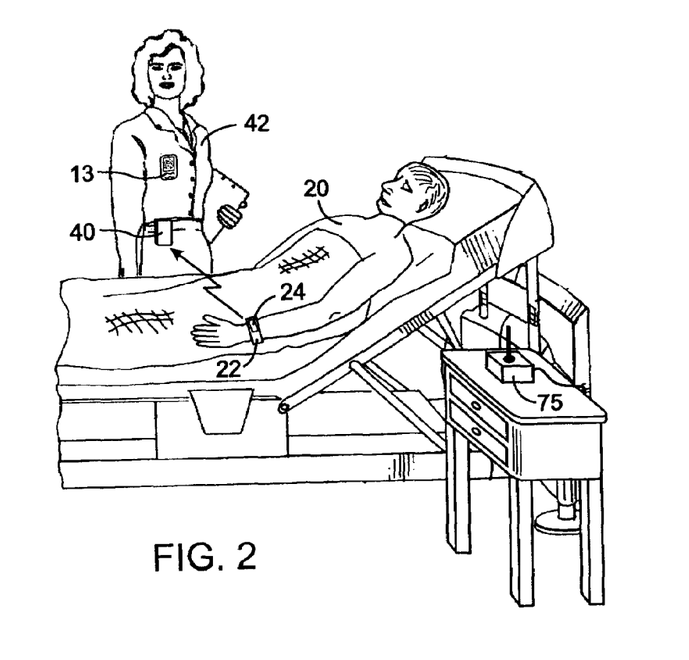
FIG. 2 depicts a healthcare worker attending to a patient, wherein a data acquisition device carried by the healthcare worker records the length of time of that visit.

However, unlike prior practice, the label 15 now is attached to a wristband 22 that contains an electronic identification device 24, which emits a radio frequency signal carrying a unique identifier for this patient, as represented in FIG. 2. That patient identifier, and a similar one to be described for a health-care worker, may comprise only numerals (i.e. a patient ID number), only alphabetic characters, or a combination of alphanumeric characters, as well as other characters. Although the exemplary identification device 24 is being described as attached to a wristband 22 fastened around the lower forearm of the patient 20, it should be understood that the identification device may be worn about other parts of the patient's body or take other forms.

The identification device 24 may be preprogrammed with the patient identifier that may be the same as or different than the standard identification number assigned to the hospital patients upon admission. That identification number also is imprinted in human readable form on the wristband, so that it can be entered into the personal computer 16 and stored in the data file in the patient records computer 11 for this patient. Alternatively, the patient identifier may be programmed into the identification device 24 by the personal computer 16 in the admissions office thereby enabling a single number or other identifier to be used for all identification purposes. In that latter case, the personal computer may download other information about the patient, such is allergies, into the identification device.

Figure 3:
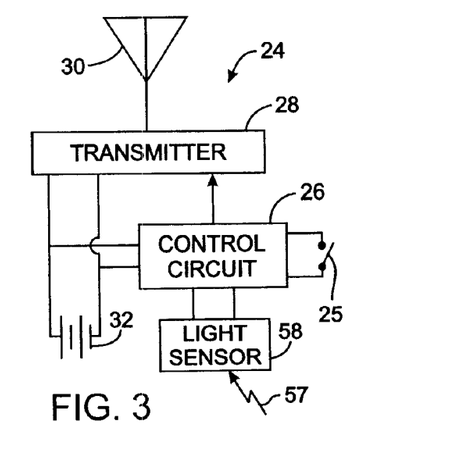
FIG. 3 is a block schematic diagram of an electronic identification device worn by the patient.

With reference to FIG. 3, the electronic identification device 24 in the wristband 22 has a control circuit 26 which governs the operation of the device and has the unique patient identifier stored therein. A switch 25, connected to the control circuit, is used to activate the identification device upon being issued to a patient. When activated, the control circuit 26 periodically sends the patient identifier to a radio frequency (RF) transmitter 28 which thereby becomes activated. The transmitter 28 modulates an RF carrier signal with the patient identifier using any standard modulation technique. The resultant first radio frequency signal is applied to an antenna 30 from which the signal radiates in an omnidirectional pattern. The components of the identification device 24 are powered by a battery 32.

Referring again to FIG. 2, while the patient 20 is within the hospital, the identification device 24 periodically transmits the first radio frequency signal 21 containing the associated patient identifier. The health-care workers in the hospital wear data acquisition devices 40 that receive the first RF signal while attending to the respective patient. For example, the data acquisition device 40 can be worn on the belt or waistband of a health-care worker 42, such as a physician, nurse, physical therapists, orderly, or laboratory technician, for example. The first RF signal from the patient's identification device 24 has an effective signal strength within only a few feet around the patient 20. Beyond that limited range the data acquisition devices 40 will not detect that first RF signal. As a result, for the data acquisition device of a given hospital worker to pickup a patient's identifier, that worker must be relatively close to the patient. That limited RF signal range reduces the likelihood of a data acquisition device 40 simultaneously receiving signals from two patients in a semi-private hospital room or in close proximity to each other in other treatment areas of the hospital. In addition, the data acquisition device 40 is configured so that as long as a signal continues to be received from one identification device 24, as determined based on the patient identifier carried by that signal, all signals from other identification devices will be ignored.

The data acquisition device 40 also may measure the strength of the RF signal received from the identification device 24 as indicating the proximity of the hospital worker to the patient. The RF signal strength can be employed to differentiate between signals that are received simultaneously from two or more identification devices 24 and select the strongest signal as likely received from the patient being treated. Even when only a single relatively weak RF signal, i.e. one having a signal strength below a defined threshold, is received, that signal may be ignored as likely originating from a patient who merely is near the medical worker and is not being treated. The RF signal strength also indicates the level of treatment being administered, as a relatively high level denotes very close proximity between the hospital worker and the patient, whereas a lower level may result from the worker merely passing near the patient.

Figure 4:
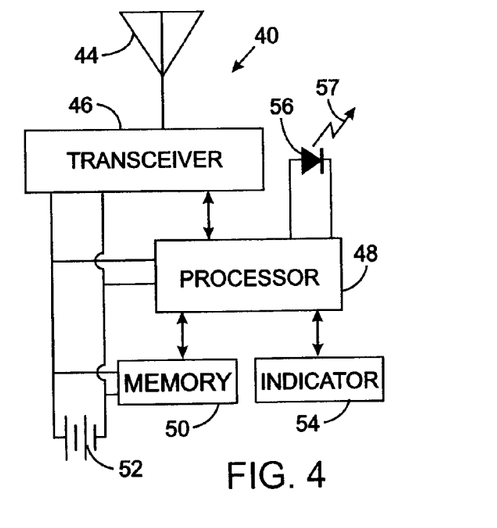
FIG. 4 is a block schematic diagram of the data acquisition device carried by the healthcare worker.

With reference to FIG. 4, the data acquisition device 40 includes an antenna 44 that is connected to a transceiver 46 which has a receiver section and a transmitter section. Upon receiving a first RF signal from a patient identification device 24, the transceiver section demodulates that signal and extracts the patient identifier. The patient identifier then is transferred to a processor 48 from which it is stored in a memory 50 of the data acquisition device 40. The processor executes a software program that also is stored in the memory 50 and which controls the operation of the data acquisition device. An indicator 54 is connected to the processor 48 and may comprise indicator lights or a liquid crystal display for presenting information about the operation of the data acquisition device to the wearer. A battery powers the components of the data acquisition device 40.

When a health-care worker 42 approaches a patient 20 as shown in FIG. 2 and the data acquisition device 40 begins receiving the patient identifier, the processor 48 starts a software based timer which measures the interval at which the health-care worker attends to the particular patient 20. That timer continues to run as long as the data acquisition device 40 continues to receive periodically a first radio frequency signal 21 containing the same patient identifier. Since the patient identification device 24 transmits the first radio frequency signal at a known interval, if a defined number of intervals pass without receiving a radio frequency signal, the data acquisition device 40 concludes that a health-care worker 42 no longer is attending to a patient. Upon reaching that determination, the processor 48 terminates the timer and stores the timer's final value into a location in memory 50 that is associated with the most recently received patient identifier. Thus, the memory 50 now contains an indication of the patient 20 and the duration of that person's recent treatment.

If the health-care worker 42 returns to attend to the same patient, a new set of storage locations within memory 50 are employed to retain the patient's identifier and another treatment time interval. When that same health-care worker 42 is in the vicinity of other patients, their respective identifiers are obtained from the first radio frequency signal transmitted by their identification devices 24 and stores along with the treatment time interval. Over the course of time, the data acquisition devices 41 worn by each health-care worker 42 who attends to patients will contain the patient identifiers for a plurality of patients along with the times that the workers attended to each of those patients.

Other information stored in the patient identification device 24 also is transmitted to the data acquisition device 40 along with the patient identifier. For example, information indicating allergies of the patient can be presented to the hospital worker on an indicator 54 of the data acquisition device 40. The data acquisition device also may receive data, such as temperature and heart rate, from portable monitors carried by the patient. Such data is stored in the data acquisition device 40 for subsequent transfer to the patient records computer 11, as will be described.

The patient identification device 24 periodically transmitting the patient identifier consumes battery power even though a hospital employee is not attending to the patient, which is the vast majority of the time for the typical patient. As a variation to conserve power, the data acquisition device 40 can include one or more infrared light emitters, such as LED 56. The processor periodically activates the light emitter, which produces a wide beam 57 of infrared light. The patient identification device 24 includes an infrared light sensor 58 that responds to receiving the light beam 57 from the data acquisition device 40 by commencing periodic transmission of the patient identifier. Those transmissions continue for a short interval after the light beam no longer is received thus tolerating short periods when the light beam may be blocked while the health-care worker is attending to the patient.

Figure 5:
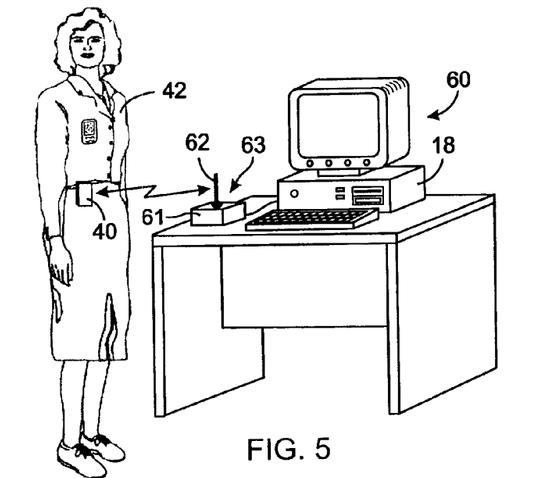
FIG. 5 illustrates the healthcare worker adjacent to a personal computer connected to hospital network and the transfer of data from the data acquisition device into the computer.
Figure 6:
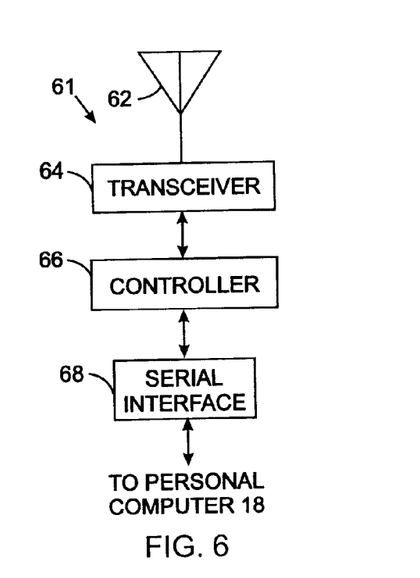
FIG. 6 is a block schematic diagram of a data interrogator connected to a personal computer in the hospital.

Referring to FIG. 1, the data stored in the data acquisition devices 40 are transferred to the computer system 10 via a plurality of data readers 63 located throughout the medical facility. The data readers 63 comprise data interrogators 61 and data collectors 75. The data interrogators 61 are connected to certain personal computers 17 and 18 which coupled to the local area network 14 in FIG. 1 and configured as patient information transfer stations 60. With reference to FIGS. 5 and 6, personal computer 18 is connected to a data interrogator 61 which acquires the stored information from the data acquisition device 40 and conveys that information to the personal computer. The data interrogator 61 has an antenna 62 connected to a transceiver 64 which exchanges commands and data with a controller 66 and passes that data through as serial interface 68 to the personal computer 18.

Periodically, such as every second or two, the interrogator 61 transmits a radio frequency signal modulated with an interrogation command. When a health-care worker 42, carrying a data acquisition device 40, is within approximately ten feet of the interrogator 61, the data acquisition device 40 responds to the interrogation command. Specifically, the interrogation command is extracted from the received radio frequency signal by the transceiver 46 in the data acquisition device 40 and sent to the processor 48 (see FIG. 4). Upon receiving an interrogation command, the processor 48 executes a software routine which reads the memory 50 to obtain a unique identifier that was assigned to the associated data acquisition device 40. This latter identifier identifies the particular data acquisition device 40 and the health-care worker 42 to whom the device was issued and thus is referred to as a "health-care worker identifier". The health-care worker identifier is sent to the transceiver 46 which modulates a radio frequency carrier with that identifier and applies the resultant radio frequency signal to the antenna 44. Then the software routine being executed by the processor 48 sequentially acquires the sets of a patient identifier and a treatment time interval stored within memory 50. Those sets of data are transferred to the transceiver 46 which sends that data via the radio frequency signal to the antenna 44. Thus, the data acquisition device 40 responds to the interrogation command by transmitting a return signal that contains its health-care worker's identifier and the patient identification and treatment time information stored within the memory 50.

Figure 7:
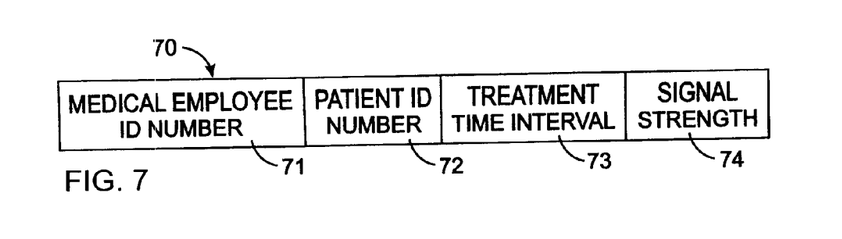
FIG. 7 is a graphical representation of data fields of a treatment event record stored within the hospital computer system.

That return signal is received by the interrogator antenna 62 and applied to the receiver section of the transceiver 64 in FIG. 6. The transceiver 64 demodulates the received signal extracting the information carried by the return signal. The health-care worker identifier and each set of a patient identifier and treatment interval time are transferred through the serial interface 68 to the personal computer 18. The personal computer temporally stores the information received from the data acquisition device as a series of treatment event records 70, one of which is represented in FIG. 7. Each treatment event record 70 comprises four data fields 71, 72, 73 and 74 respectively containing the health-care worker identifier, a patient identification, a treatment time interval, and a measurement of the strength of the RF signal from the patient's identification device 24. After all the patient treatment information has been acquired from the data acquisition device 40, the personal computer 18 transfers that information over the local area network 14 to the patient records computer 11.

Alternatively, the data interrogator may comprise a cable connected to the personal computer 18 and a software routine that is executed by that personal computer. The cable is connected temporarily to the data acquisition device 40. The software routine issues the interrogation command via the cable to the data acquisition device and obtains the patient treatment information.

Other types of data interrogators that perform this function can be employed. For example referring to FIG. 10, the data readers 63 also comprise a plurality of wireless data collectors 75 connected to the local area network 14. Those data collectors 75 are located, on the ceilings of hallways 76 for example, throughout the areas of the medical facility 77 in which patients are treated so that the medical worker's data acquisition device 40 always will be within range of at least one data collector 75. Alternatively, a data collector 75 may be located adjacent a patient's bed, as shown in FIG. 2. Now, as the data acquisition device 40 completes timing a health-care worker's visit to a patient's room 78, the data associated with that visit is immediately transmitted to a wireless data collector 75.

Figure 11:
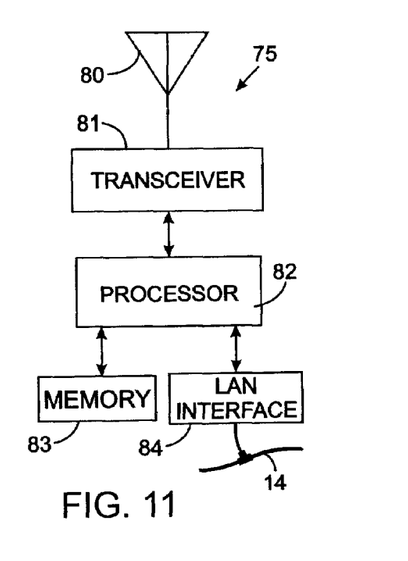
FIG. 11 is a block schematic diagram of one of a plurality of monitors shown in FIG. 10 and located throughout the medical facility.

With reference to FIG. 11, each data collector 75 has an antenna 80 connected to a transceiver 81 which exchanges commands and data with a processor 82, such as a microcomputer, for example. The data gathered by the data collector is stored temporarily by the processor 82 in a memory 83 as the treatment event records 70. That data, along with an identification of the particular data collector 75, then is periodically transferred via a LAN interface 84 over the local area network 14 to the patient records computer 11.

The patient records computer 11 parses the treatment information, received from the data readers 63, based on the patient identifiers and stores that information in separate data records for each patient. Each such record for a given patient has data showing which health-care worker treated that patient and the duration of each treatment. This patient treatment information then can be analyzed to determine the total time of treatment each patient received and the amounts of time that the particular patient was treated by each different class of health-care workers, such as physicians, nurses, nursing assistants, orderlies, X-ray technicians, etc. The general patient information stored in the patient records computer 11 designates the nursing unit to which an inpatient is assigned. This enables the acquired treatment information to be further analyzed to determine the magnitude of nursing care being provided at each nursing unit within the medical facility and thus forecast staffing requirements on a daily basis.

The patient treatment information also is transferred to the employee time and attendance computer 12 which tabulates the information based on the health-care worker identifier associated with each treatment event record 70 from the data acquisition devices 40. Thus, a record for a particular health-care worker stored within the memory of the time and attendance computer 12 contains information identifying each patient that the respective health-care worker treated and the amount of time of such treatments. This information can be analyzed to determine the total amount of treatment provided by a particular health-care worker. The employee records in the time and attendance computer 12 may specify that a given health-care worker is assigned to a particular hospital treatment unit, such as a given nursing unit, the emergency room, medical imaging facility, physical therapy department, and the like. That health-care worker data along with the patient treatment information enables analysis of the patient care provided at each hospital treatment unit.

For example the acquired data for a particular employee can be analyzed to determine whether that person is attending to patients to whom he or she is not assigned. The treatment data also can be analyzed to track the progress and the experiences of a physician intern or other employee in training.

Figure 8:
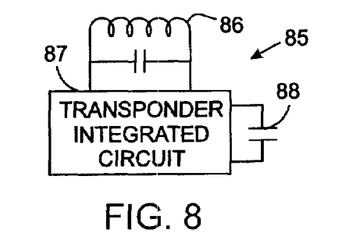
FIG. 8 is a block schematic diagram of another embodiment of an electronic identification device worn by the patient.

FIG. 8 depicts second type of electronic patient identification device 85 for incorporation into the wristband 22 of the patient 20. This second identification device is passive in that it does not require a power source, such as a battery. Instead, the second patient identification device 85 comprises a conventional radio frequency transponder tag, such as the type that is commonly used to identify products or used as a key-card of a building entry system. The second patient identification device 85 has an antenna 86 that is part of a tuned, resonant circuit connected to a transponder integrated circuit 87 which may be any one of a number of commercially available devices, such as one of a family of products available from Texas Instruments Incorporated, Dallas, Tex., USA. The transponder integrated circuit 87 is powered by energy derived from a radio frequency signal received at antenna 86 and used to store a charge on a capacitor 88. That stored charge provides a voltage for powering the electronic circuits. Because the second patient identification device 85 does not require power from a battery, it can be utilized with patients requiring long term care or who will be permanent residents of a nursing facility.

Figure 9:
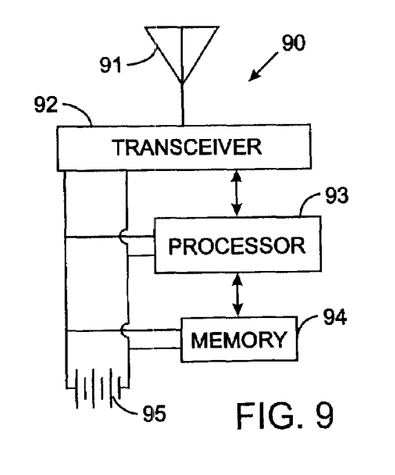
FIG. 9 is a block schematic diagram of another embodiment of a data acquisition device worn by the healthcare worker.

The second patient identification device 85 is used in conjunction with a second type of data acquisition device 90 represented in FIG. 9 and carried by a health-care worker 42. That second data acquisition device 90 has an antenna 91 which is connected to a radio frequency transceiver 92. The transceiver 92 exchanges data with and is controlled by a processor 93 that interfaces with a memory 94. The components of the data acquisition device 90 are powered by a battery 95.

A second data acquisition device 90 periodically, every second or so, emits a second radio frequency signal that has an effective range of approximately ten feet extending radially from the antenna 91. When a second patient identification device 85 is within in that effective range, the transponder integrated circuit 87 becomes energized by power derived from that second radio frequency signal. In response to the receipt of a second radio frequency signal, the second patient identification device 85 replies by emitting the first radio frequency signal that carries the unique patient identifier that is stored within the transponder integrated circuit 87. Upon receiving a valid reply from a second patient identification device 85, the transceiver 92 demodulates that reply signal, extracting the unique patient identifier, which then is passed to the processor 93 which stores it in a location in memory 94. Upon the receiving a different patient identifier, the processor 93 starts a timer in a similar manner to that described previously with respect to the first data acquisition device 40. The timer continues to run as long as the second data acquisition device 90 continues to receive replies from a transponder. When the replies cease, the processor 93 stops the timer and records the final value within a location in memory 94 that is associated with the respective patient identifier. This process is repeated each time the data acquisition device 40 receives a reply from a different transponder type second patient identification device 85.

In close proximity to a data interrogator 61, the second data acquisition device 90 receives an interrogation command carried by the radio frequency signal from the data interrogator. The second data acquisition device 90 responds to the interrogation command by transferring its health-care worker identifier and the acquired patient treatment data from the memory 94 to the data interrogator 61 in the same manner as described previously with respect to the first data acquisition device 40. The patient treatment data is conveyed to the patient records computer 11 and the time and attendance computer 12 for storage and analysis also as described above.

Patient Monitoring

Figure 10:
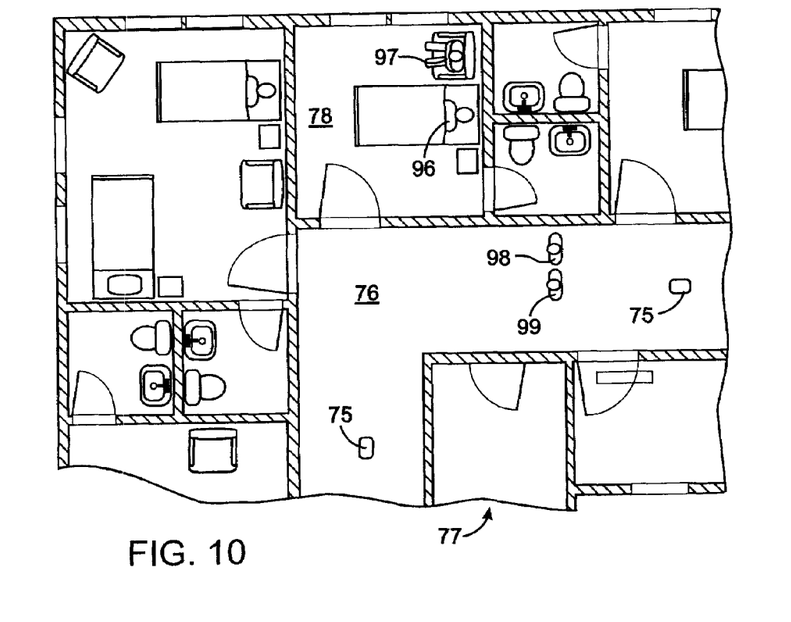
FIG. 10 is a diagram of rooms on part of a floor in a medical facility in which a patient supervision monitoring system has been installed.

With reference to FIG. 10, various medical situations require that a particular patient 96 be continuously observed by a health-care worker 97. For example, some ailments and treatments require an immediate response to a change in the patient's condition. Other patients with suicidal tendencies may also require constant observation. An orderly or license practical nurse may be assigned to sit next to or immediately outside the room of this type of patient.

The present monitoring system can be employed to ensure that there always is a health-care worker 97 near a patient 96 who must be observed continuously. The data acquisition device 40 of the observing health-care worker will record data indicating the proximity to the patient. Therefore, should the health-care worker 97 leave the vicinity of the patient 96 being monitored, the recorded data will indicate that absence. A given health-care worker may leave the vicinity of the patient under observation only upon being relieved by another health-care worker. In which case a different data acquisition device 40 will record that the other health-care worker is observing the patient. Any lapse in the continuous patient observation can be detected by analyzing the information gathered from all the data acquisition devices 40.

When the medical facility has data collectors 75 located throughout the patient treatment areas, the data acquisition device 40 of the observing health-care worker 97 will be interrogated at regular intervals while the worker is on duty. Thus during a period of time that the patient 96 is to be monitored, any absence of that health-care worker from the vicinity of the patient 96 will be immediately reported to the patient records computer 11, which responds by alerting a nursing supervisor via message sent to a designated personal computer 16-18. The alarm message may be issued only after the health-care worker has been absent from the patient for a predefined time period, e.g. one minute, to tolerate signal interference and to permit the worker to step outside the room for a short interval.

In other instances, a health-care worker 98 is required to escort a patient 99 either whenever the patient is outside the room containing the assigned bed or when the patient is in specific areas of the medical facility. The present monitoring system also can be used to ensure that such escorting occurs. This function can be implemented by a version of the data collector 75 that also may be able to receive patient identifiers directly from the identification devices 24 worn by patients, as well as data from worker data acquisition devices 40. With continuing reference to FIG. 10, when a patient 99 travels some distance from his/her assigned bed, a data collector 75 in another area of the medical facility receives a wireless signal containing the patient's identifier. When that data and the identification of the particular data collector 75 is transmitted to the patient records computer 11 (FIG. 1), that computer recognizes that the patient 99 is away from the vicinity of the assigned room. That event in and of itself is not a problem provided that a healthcare worker is escorting the patient.

If the traveling patient 99 is being escorted, a data acquisition device 40 for a health-care worker 98 also receives the identifier signal from that patient's identification device 24. The data acquisition device 40 transfers the patent's identifier to the same data collector 75 which received the patent identifier directly from the identification device 24 worn by that patient 99. The data collector 75 sends the information acquired from the health-care worker's data acquisition device 40 to the patient records computer 11. As long as the same patient identifier is received from both the patient's identification device 24 and a health-care worker's data acquisition device 40, the patient records computer 11 determines that the two people are in close proximity to each other. However, when the patient records computer 11 receives a patient identifier only from a patient identification device 24, via, a data collector 75 remote from the patient's assigned room, a conclusion is made that the patient is unescorted away from the vicinity of his/her assigned bed. As a result the patient records computer 11 sends an alarm message to a designated personal computer 16-18 to alert nursing personnel responsible for that patient. The alarm message may be issued only if a corresponding data is not received from a health-care worker's data acquisition device 40 for a predefined period of time, e.g. one minute, after the receipt of data from the patient identification device 24, to allow for signal interference and permit the worker to leave a patient momentarily.

In another embodiment of the present patient monitoring system, the data collectors 75 throughout the medical facility shown in FIG. 5 periodically emit separate interrogation signals for both the transponder-type, patient identification devices 85 and the data acquisition devices 40 carried by health-care workers. Replies to those interrogation signals enable the locations of patients and health-care workers to be determined.

For example, a given data collector 75 emits a first type of interrogation signal for the patient identification devices 85 and begins a timer which measures the interval until a response in received. The duration of that interval is directly related to the distance between the data collector 75 and the patient 99 associated with the responding identification device. That time interval measurement, the patient identifier carried by the response, and the identity of the receiving data collector 75 are all sent in a message to the patient records computer 11. Soon thereafter, other nearby data collectors 75 emit similar interrogation signals and receive responses from the same patient identification device 85. The other data collectors 75 send similar sets of data to the patient records computer 11. Data collectors 75 are located sufficiently close together so that a patient always is within the range of at least three data collectors. Therefore, the patient records computer 11 will receive messages from at least three data collectors 75 identifying the same patient. The three time intervals in those messages enable the patient records computer 11 to ascertain the distance that the patient 99 is from each of those data collectors 75 and the intersection of those distances indicates the location of the patient.

Each data collector 75 also emits a second type of interrogation signal for the data acquisition devices 40 carried by health-care workers 98. Responses to those interrogation signals from a given data acquisition device 40 also are received by at least three data collectors 75. Those data collectors then send messages to the patient records computer 11 with each conveying a response interval measurement and an identification of the respective data collector. These messages enable the patient records computer 11 to determine the location of associated health-care worker 98 in the same manner as used to determine the patient's location.

For a patient identified in the patient records computer 11 as requiring continuous monitoring or for a patient within an area in which an escort is required, a determination is made whether a health-care worker is nearby. Specifically, the location of such a patient is compared to the location of a particular health-care worker assigned to that patient. If the two locations are within a given distance of each other, the patient records computer 11 concludes that this patient is being properly monitored. In some cases, a particular health-care worker is not assigned to that patient and the presence of any health-care worker within a given distance of the patient is all that is required.

The foregoing description was primarily directed to preferred embodiments of the invention. Although some attention was given to various alternatives within the scope of the invention, it is anticipated that one skilled in the art will likely realize additional alternatives that are now apparent from disclosure of embodiments of the invention. Accordingly, the scope of the invention should be determined from the following claims and not limited by the above disclosure.

What is claimed is:

1. A method for monitoring supervision of a patient by health-care workers, said method comprising:
   issuing an identification device to the patient wherein the identification device wirelessly emits a first signal in response to at least one of termination of a time period and receipt of a wireless signal;
   issuing a data acquisition device to a health-care worker, wherein the data acquisition device emits a second signal; and
   in response to the first signal and the second signal, determining information related to attendance of the health-care worker near the patient.

2. The method as recited in claim 1 further comprising the data acquisition device receiving the first signal, and wherein the second signal indicates receipt of the first signal.

3. The method as recited in claim 2 wherein determining information comprises receiving the second signal and deriving therefrom information related to attendance of the health-care worker near the patient.

4. The method as recited in claim 1 wherein determining information related to attendance comprises determining whether the health-care worker has been absent from being near the patient during a predetermined time period.

5. The method as recited in claim 1 wherein determining information related to attendance comprises determining whether the health-care worker has been absent from being near the patient.

6. The method as recited in claim 5 further comprising issuing an alarm when the health-care worker has been absent from being near the patient.

7. The method as recited in claim 5 wherein an alarm is emitted when the health-care worker is absent for a predefined period of time.

8. The method as recited in claim 1 wherein the second signal is wireless.

9. The method as recited in claim 1 further comprising in response to the second signal, determining whether the health-care worker is proximate to the patient in response to the patient being near a given location.

10. The method as recited in claim 9 wherein the given location is remote from a bed assigned to the patient.

11. The method as recited in claim 1 further comprising:
    determining, in response to the first signal, a first location related to the patient; and
    determining, in response to the second signal, a second location related to the health-care worker.

12. The method as recited in claim 11 further comprising producing from the first location and the second location an indication of proximity of the health-care worker to the patient.

13. A method for monitoring supervision of a patient by health-care workers, said method comprising:
    issuing an identification device to the patient, wherein the identification device wirelessly emits a first signal that identifies the patient;
    issuing a data acquisition device to a health-care worker, wherein the data acquisition device receives the first signal and, upon interrogation, wirelessly emits a second signal indicating whether the first signal was received; and
    interrogating the data acquisition device to obtain the second signal; and
    in response to contents of the second signal, determining whether the health-care worker has been absent from being near the patient.

14. The method as recited in claim 13 wherein the determining concludes whether the health-care worker has been absent from being near the patient during a predetermined time period.

15. The method as recited in claim 13 further comprising issuing an alarm when the health-care worker has been absent from being near the patient.

16. The method as recited in claim 13 wherein an alarm is emitted when the health-care worker is absent from the patient for a predefined period of time.

17. The method as recited in claim 13 further comprising in response to the second signal, determining whether the health-care worker is absent from being near the patient while the patient is proximate to a given location which is remote from a bed assigned to the patient.

18. A method for monitoring supervision of a patient by health-care workers, said method comprising:
    issuing an identification device to the patient wherein the identification device responds to at least one of termination of a time period and receipt of an interrogation signal by emitting a first signal that identifies the patient;
    issuing to a health-care worker a data acquisition device that emits a second signal;
    providing a data reader at a given location for receiving at least one of the first signal and the second signal; and
    in response to the data reader, determining whether the health-care worker is proximate to the patient while the patient is near the given location.

19. The method as recited in claim 18 wherein the data reader is adapted to receive both the first signal and the second signal; and determining whether the health-care worker is proximate to the patient is performed in response to whether both the first signal and the second signal are received by the data reader.

20. The method as recited in claim 18 wherein the data reader is adapted to receive only the second signal; and determining whether the health-care worker is proximate to the patient is performed in response to the second signal being received by the data reader.

21. The method as recited in claim 18 further comprising emitting an alarm when a determination is made that the health-care worker is not proximate to the patient.

22. The method as recited in claim 18 wherein the first signal and the second signal are wireless signals.

23. The method as recited in claim 18 further comprising:
the data reader receiving the first signal from the identification device;
deriving a first location in response to the first signal;
the data reader receiving the second signal from the data acquisition device;
deriving a second location in response to the second signal; and
producing from the first location and the second location an indication of proximity of the health-care worker to the patient.

24. The method as recited in claim 18 further comprising:
the data reader interrogating the identification device to obtain the first signal;
deriving a first location in response to the first signal;
the data reader interrogating the data acquisition device to obtain the second signal;
deriving a second location in response to the second signal; and
producing from the first location and the second location an indication of proximity of the health-care worker to the patient.

* * * * *